(12) United States Patent
Stearns et al.

(10) Patent No.: US 8,772,680 B2
(45) Date of Patent: *Jul. 8, 2014

(54) ADAPTIVE TEMPERATURE CONTROLLER

(71) Applicant: Valco Instruments Company, L.P., Houston, TX (US)

(72) Inventors: Stanley D. Stearns, Houston, TX (US); Huamin Cai, Houston, TX (US); Chris S. Cowles, Houston, TX (US)

(73) Assignee: Valco Instruments Company, L.P., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/085,263

(22) Filed: Nov. 20, 2013

(65) Prior Publication Data

US 2014/0076885 A1    Mar. 20, 2014

Related U.S. Application Data

(63) Continuation of application No. 12/257,715, filed on Oct. 24, 2008, which is a continuation of application No. 11/685,325, filed on Mar. 13, 2007, now Pat. No. 7,442,902.

(60) Provisional application No. 60/767,236, filed on Mar. 13, 2006.

(51) Int. Cl.
*H05B 1/02*    (2006.01)

(52) U.S. Cl.
USPC ........... 219/490; 219/497; 219/505; 338/22 R (58) Field of Classification Search
USPC ................. 219/490, 497, 499, 501, 504, 505; 338/22 R; 374/1, 100, 102
See application file for complete search history.

(56) References Cited

U.S. PATENT DOCUMENTS

| 5,105,067 | A | 4/1992 | Brekkenstran et al. |
| 5,553,622 | A | 9/1996 | McKown et al. |
| 5,755,670 | A | 5/1998 | McKown et al. |
| 5,793,022 | A | 8/1998 | Klinck |

(Continued)

FOREIGN PATENT DOCUMENTS

| CN | 1930917 A | 3/2007 |
| EP | 1262649 B1 | 4/2002 |

(Continued)

OTHER PUBLICATIONS

Uta Muller, European Patent Office Examination Report—EP 09 822 380.3-2206, Aug. 29, 2012, 6 pages, European Patent Office, Munich, Germany.

(Continued)

*Primary Examiner* — Brian Jennison
(74) *Attorney, Agent, or Firm* — Crain, Caton & James, P.C.; James E. Hudson, III (57) ABSTRACT

The adaptive temperature controller system includes a device for measuring resistance, an electrically-conductive material, a power supply, and a device for controlling power. In operation, the controller determines the resistance of material at one or more temperatures and therefore determines the resistance of the material through a range of operating temperature. Based on such determination so long as voltage and power are known, the resistance of the material, and therefore its temperature, are known. As a result the voltage or power may be instantly varied to produce near infinite control over material temperature.

8 Claims, 7 Drawing Sheets

(56) References Cited

U.S. PATENT DOCUMENTS

| | | | |
|---|---|---|---|
| 5,808,178 | A | 9/1998 | Rounbehler et al. |
| 6,252,209 | B1 | 6/2001 | Liepold |
| 6,519,546 | B1 | 2/2003 | Eryurek et al. |
| 7,193,187 | B2 | 3/2007 | Chen |
| 7,442,902 | B2 | 10/2008 | Stearns et al. |
| 2005/0205549 | A1 | 9/2005 | Crawford et al. |
| 2007/0210285 | A1 | 9/2007 | Stearns et al. |
| 2009/0045187 | A1 | 2/2009 | Stearns et al. |

FOREIGN PATENT DOCUMENTS

| | | | |
|---|---|---|---|
| JP | 2001505690 | A | 4/2001 |
| WO | 9100131 | A1 | 1/1991 |
| WO | 2007106803 | A2 | 9/2007 |

OTHER PUBLICATIONS

Graime Evans, IP Australia Patent Examination Report No. 1—2009 307982, Apr. 9, 2013, 3 pages, IP Australia, Government of Australia, Woden, ACT, Australia.

Jack Redfern, Response to IP Australian Patent Examination Report No. 1—2009 307982, May 16, 2013, 48 pages, ShelstoniP, Syndey, NSW, Australia.

IP Australia Notice of Acceptance—2009 307982, Jun. 7, 2013, 2 pages, IP Australia, Government of Australia, Woden, ACT, Australia.

Abdulmalik Lawal, Response to EP Office Examination Report—EP 09 822 380.3 -2206, Nov. 5, 2012, 16 pages, Murgitroyd & Co., Ltd., Glasgow, UK.

First Office Action—China Patent Application 200980152498.0, Dec. 4, 2012, 5 pages, State Intellectual Property Office, People's Republic of China, Haidan District, Beijing, China.

Uta Muller, Supplementary European Search Report—EP 09 822 380.3-2206, Feb. 2, 2012, 9 pages, European Patent Office, Munich, Germany.

Lars Theunissen, Summons to attend oral proceeding pursuant to Rule 115(1) EPC (EPO Application 07758413.4), Oct. 27, 2011, 7 pages, European Patent Office, Munich, Germany.

Zhenwen Wang, Accurate modeling of thin film resistor up to 40 GHz, ESSDERC 2002: 32nd European Solid-Slate Device Research Conference, Sep. 24-26, 2002, 4 pages (pp. 307-310), Firenze, ISBN 88-900847-8-2.

D. H. Galvan, Effect of Silver in Y1 Ba2Cu3O7-x samples, Journal of Materials Science, val. 29, No. 10, 1994, 6 pages (pp. 2713-2718), Heidelberg, Allemagne, ISSN: 0022-2461.

Lars Theunissen, Communication pursuant to Article 94(3) EPC (EPO Application 07758413.4), Aug. 10, 2011, 4 pages., European Patent Office, Munich, Germany.

Phillipe Mallet, Communication pursuant to Article 94(3) EPC (EPO Application 07758413.4), Dec. 15, 2010, 4 pages, European Patent Office, Munich, Germany.

First Office Action of Jan. 7, 2011—Chinese Patent Application 200780008877.3, Jan. 7, 2011, 3 pages, State Intellectual Property Office, People's Republic of China, Beijing, China.

Ken Wieder, International Preliminary Report on Patentability (PCT/US09/56963), Jan. 11, 2011, 7 pages, United States Patent and Trademark Office as Search Authority, Alexandria, Virginia, US.

Ken Wieder, Notification of Transmittal of International Preliminary Report on Patentability (PCT/US09/56963), Jan. 11, 2011, 2 pages, United States Patent and Trademark Office as Search Authority, Alexandria, Virginia, US.

Lee W. Young, Written Opinion of the International Search Authority (PCT/US09/56963), Oct. 22, 2009, 5 pages, United States Patent and Trademark Office as Search Authority, Alexandria, Virginia, US.

Lee W. Young, International Search Report (PCT/US09/56963), Oct. 22, 2009, 2 pages, United States Patent and Trademark Office as Search Authority, Alexandria, Virginia, US.

Mark H. Paschall, International Search Report—PCT/US07/63861, Aug. 7, 2008, 2 pages, United States Patent and Trademark Office as International Search Authority, Alexandria, Virginia US.

Mark H. Paschall, Written Opinion—PCT/US07/63861, Aug. 7, 2008, 4 pages, United States Patent and Trademark Office as International Search Authority, Alexandria, Virginia US.

Mark H. Paschall, International Preliminary Examination Report—PCT/US07/63861, Feb. 26, 2009, 3 pages, United States Patent and Trademark Office as International Search Authority, Virginia US.

Second Office Action—CN2009801524498.0, Jul. 15, 2013, 4 pages, State Intellectual Property Office, People's Republic of China, Beijing, China.

Taku Kakizaki, Reasons for rejection—JP2011-533205, Oct. 3, 2013, 2 pages, Japanese Patent Office, Tokyo, Japan.

First Office Action—CN2009801524498.0, Dec. 4, 2012, 5 pages, State Intellectual Property Office, People's Republic of China, Beijing, China.

ADAPTIVE TEMPERATURE CONTROLLER

CROSS REFERENCE TO RELATED APPLICATIONS

This application is a continuation of U.S. Pat. No. 8,642,931 issued Feb. 4, 2014 for "Adaptive Temperature Controller" and is a continuation in part of U.S. Pat. No. 7,442,902 issued Oct. 28, 2008 for "Adaptive Temperature Controller," priority to which is hereby claimed, and claims the benefit of U.S. Provisional Patent Application No. 60/767,236 entitled, "Adaptive Temperature Controller" filed on Mar. 13, 2006 in the United States Patent and Trademark Office.

STATEMENT REGARDING FEDERALLY SPONSORED RESEARCH OR DEVELOPMENT

Not Applicable.

BACKGROUND OF THE INVENTION

1. Field of the Invention

This invention pertains to a device for simultaneously controlling the temperature of a heating element and monitoring its temperature. In particular, the device pertains to controlling the temperature of a heating element for use in chromatographic analysis including heating of columns, detectors and other components, although it may be used in any system wherein precise heating through a range of temperatures is desired.

2. Description of the Related Art

An adaptive temperature controller for use with any electrically-conductive material is disclosed. It is often necessary to maintain portions of test equipment or other items above ambient temperature. This has been accomplished in the prior art with various temperature controllers. It is well known to provide a source of heat that is easily controlled. Most often heat is transferred from a conductive element. In the prior art the temperature of such conductive element was monitored by a separate device, often a Resistance Temperature Detector (RTD). However this requires multiple parts, increasing the space consumed by such equipment, the weight of such equipment, and its cost. Additionally, such systems often were unable to produce rapid temperature changes. Moreover, heating of equipment was not uniform and often was not sufficiently fast.

It would therefore be a desirable improvement to have a temperature controller with fewer parts that likely would reduce weight, space and cost, would provide uniform heating, and would be capable of rapid heating and cooling.

SUMMARY OF THE INVENTION

The adaptive temperature controller disclosed herein includes a device for measuring electrical resistance, an electrically-conductive material, and a power supply. In operation, the controller determines the resistance of the electrically-conductive material at one or more predetermined temperatures and is able to determine the corresponding resistance of the electrically-conductive material at other temperatures within a temperature range and to apply the voltage or current necessary to obtain such resistances. The predetermined (calibration) temperatures of the electrically-conductive material may be determined by using a temperature sensor or by approximation based on ambient air temperature. As a result, the voltage or power may be instantly varied to produce near infinite control over material temperature.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only typical preferred embodiments of the invention and are therefore not to be considered limiting of its scope as the invention may admit to other equally effective embodiments.

DETAILED DESCRIPTION OF THE PREFERRED EMBODIMENT

Figure 1A:
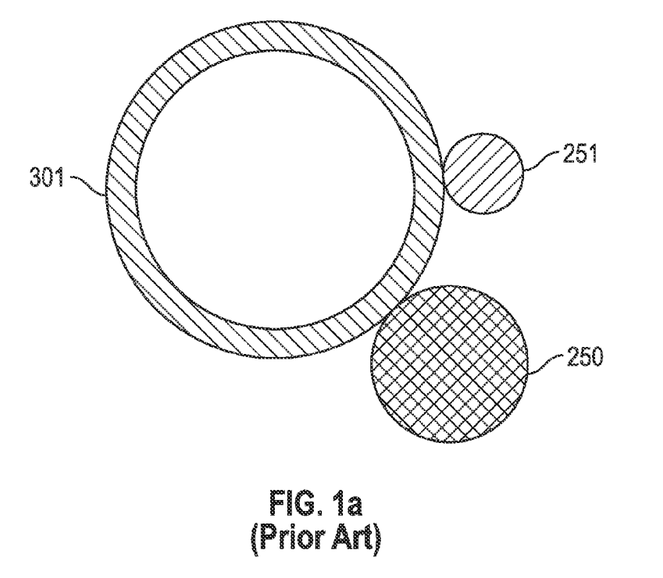
FIG. 1a depicts a cross-sectional view of one embodiment of the prior art.
Figure 1B:
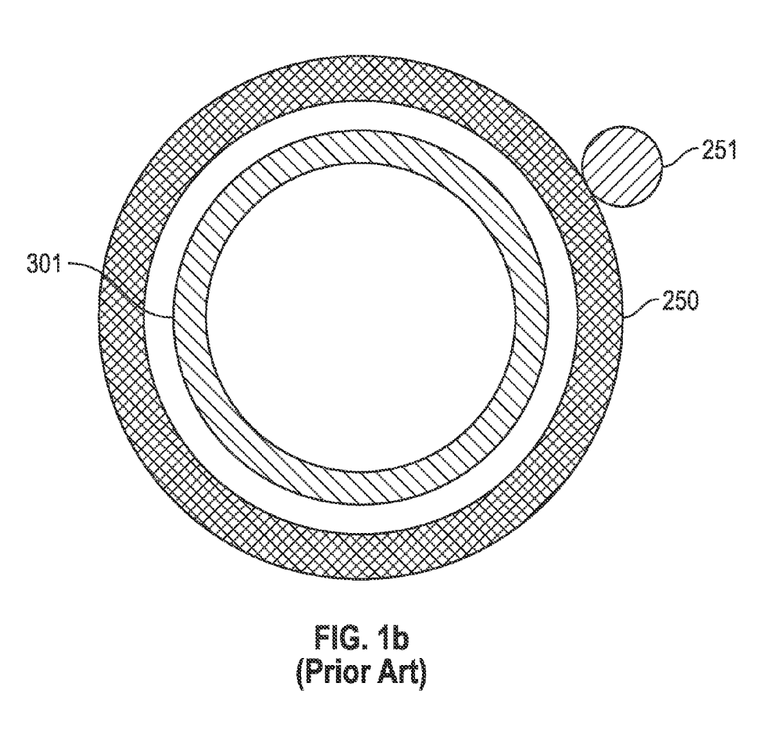
FIG. 1b depicts a cross-sectional view of another embodiment of the prior art.

As depicted in FIGS. 1a and 1b, temperature controllers are known where a conductive element 250 and a sensor 251 were placed in proximity to or about the component 301 of a system 300 to respectively heat and monitor the temperature of element 301. It is well known to provide a source of heat that is easily controlled. Most often heat is transferred from a conductive element 250 to be subsequently distributed to element 301. The conductive element 250 may be placed adjacent (FIG. 1a) or surrounding (FIG. 1b) element 301. In the prior art the temperature of conductive element 250 was monitored by a separate sensor 251, often a RTD. This requires multiple parts, increasing the space consumed by such equipment, the weight of such equipment, and its cost.

An electrically-conductive material 50 may be used to heat a component 101 of a system 100, such as a detector or column in the case of chromatographic analysis, directly or indirectly. In the case of chromatographic analysis, the component 101 may be a chromatographic column 102 of chromatographic system 100, which includes an analyte injector 103 and a detector 104. In direct heating, depicted in FIG. 2a, the component 101, a column, of the system 100 is composed, at least in part, of electrically-conductive material 50, shown in cross-section in FIG. 2b. In indirect heating, depicted in FIG. 3a, the component 101 of the system 100 is contacted by electrically conductive material 50, shown in cross section in FIG. 3b. In indirect heating, the component 101 contacted or encircled may be a detector, a column, or other device. In FIG. 3a, component 101 is again a column. The temperature to which the electrically-conductive material 50 heats the element, the rate of heating, and the duration of heating at any temperatures, is controlled by adaptive temperature controller 10. In alternative embodiments, the adaptive temperature controller may be used in conjunction with any system wherein precise temperature control throughout a range is desired.

Figure 2A:
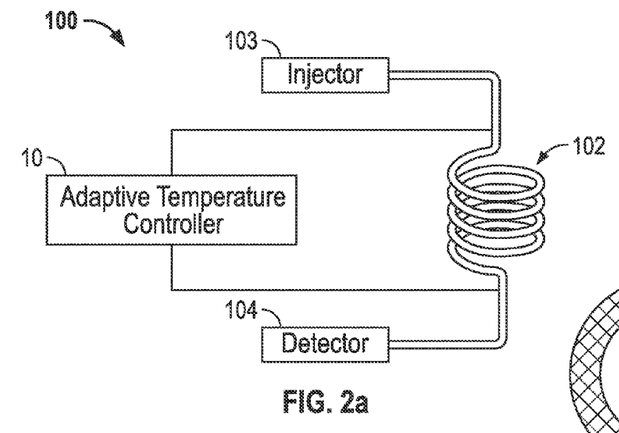
FIG. 2a depicts direct heating of the component by the adaptive temperature controller.
Figure 2B:
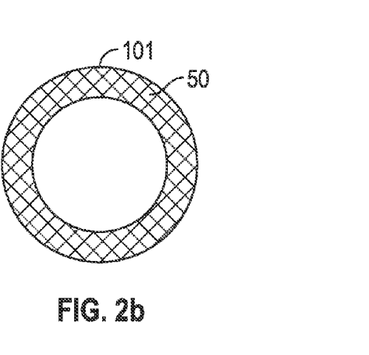
FIG. 2b depicts the component heated by direct heating controlled by the adaptive temperature controller.
Figure 3A:
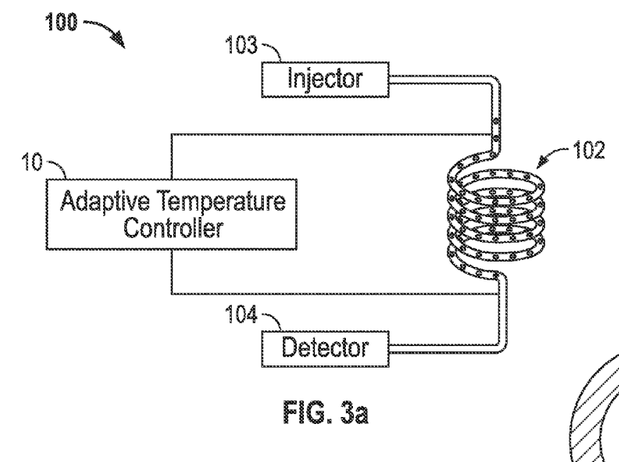
FIG. 3a depicts indirect heating of the component by the adaptive temperature controller.
Figure 3B:
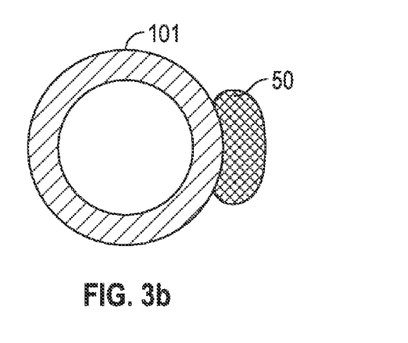
FIG. 3b depicts the component heated by indirect heating controlled by the adaptive temperature controller.
Figure 10:
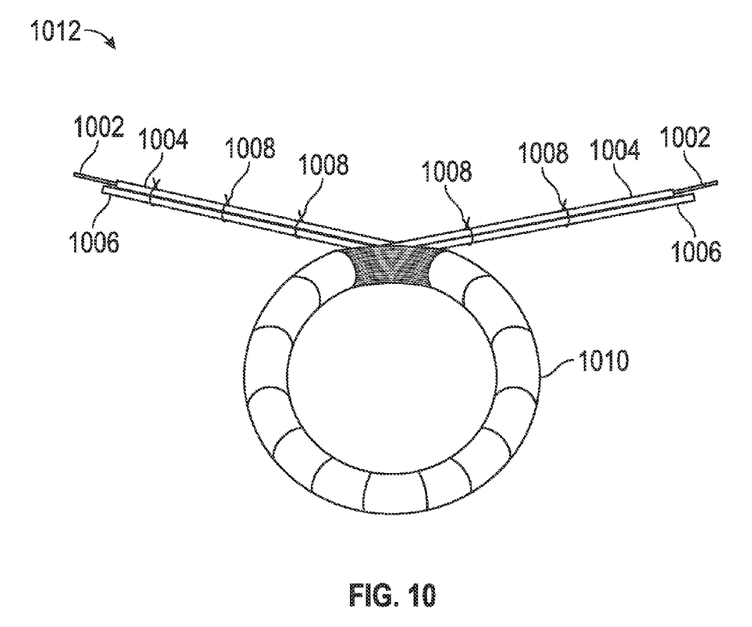
FIG. 10 depicts a chromatographic column assembly for heating with the adaptive temperature controller of the present disclosure.

As depicted in FIGS. 2a and 3a, in operation, the electrically-conductive material 50 used in conjunction with adaptive temperature controller 10 has a known electrical resistance as a function of temperature. Adaptive temperature controller 10 is in electrically conductive communication with electrically-conductive material 50. The relationship between resistance and temperature for electrically-conductive material 50 may be obtained by adaptive temperature controller 10 by application of an equation or by interpolation from a table of such data. Since the electrical resistance of an electrically-conductive material 50 is known as a function of temperature, the temperature of the electrically-conductive material 50 can be determined by a dynamic measurement of the electrical resistance of electrically-conductive material 50. The temperature of electrically-conductive material 50 may therefore be controlled by virtue of the current (or voltage or both) applied to electrically-conductive material 50. In the preferred embodiment, electrically-conductive material 50 is nickel.

Where the electrically-conductive material 50 is a column for chromatographic separation, the electrically-conductive material 50 may be constructed from a commercial fused silica column coated in nickel using an electroplating process. A thin layer of polyamine may be added over the nickel coating for insulation. Alternatively, such as illustrated in FIG. 10, the electrically-conductive material 50 may be a wire 1002 of nickel or containing nickel, such as a nickel-iron alloy, which may be jacketed in insulation 1004, placed parallel to or adjacent to a fused silica column 1006, the two of which are then retained together and maintained adjacent, such as by being wrapped with a small thread of fiberglass or another, durable binding 1008. In either embodiment, the column 1006 and wire 1002 are coiled, preferably in a circular coil, and the coil bundled and wrapped in a heat conducting outer jacket 1010, such as with aluminum foil, to form a chromatographic column assembly 1012. Two leads may be spotwelded to each end of the electrically-conductive material 50 to provide two sets of wires, thus providing a four (4) wire resistance measurement system in order to increase the accuracy of the resistance measurement. Because the entire wire 1002 is heated to a consistent temperature and because the coil of column and wire is bundled and wrapper, consistent heating throughout the coil is obtained.

In instances when the resistance of the electrically-conductive material 50 is not immediately known, but its normalized resistance characteristic is known, such as in the case of an unknown length or diameter of nickel wire, the adaptive temperature controller 10 may be calibrated for use with electrically-conductive material 50 by measurement of the resistance of electrically-conductive material 50 at one or more known temperatures. A uniform temperature throughout an electrically-conductive material 50 may be obtained by heating the electrically-conductive material 50 in an oven. The scale factor derived by dividing the measured resistance value of electrically-conductive material 50 by the normalized resistance value of the material from which electrically-conductive material 50 is composed at the reference temperature may then be applied to the normalized resistance characteristic to determine the resistance of electrically-conductive material 50 at any particular temperature.

Unlike the prior art by use of adaptive temperature controller 10, any length or size of electrically-conductive material 50 may be used for heating. Providing use of any length or size of material is of significance as dimensions of heating materials may vary due to fluctuations in materials and cutting techniques. Moreover, unlike the prior art, separate temperature sensors are unnecessary as temperature may be determined at any time by measurement of the voltage and current applied.

It is desirable that adaptive temperature controller 10 include a learning step to determine the responsiveness of the resistance, and therefore temperature, of electrically-conductive material 50 to change in current, voltage or power. Determination of responsiveness is important to reduce or eliminate overshoot and/or undershoot of temperature by adaptive temperature controller 10. Having determined the resistance of electrically-conductive material 50 at known temperatures, adaptive temperature controller 10 may then determine the rate of temperature increase relative to an increase in voltage, current or power by various methods known in the art, including by analyzing data pertaining to the temperature increase of the electrically-conductive material 50 in the oven per unit time compared to the temperature increase in the oven. An electrically-conductive material 50 having a large mass will exhibit a lower rate of rise of temperature proportionate to increase in current, voltage or power. Likewise, an electrically-conductive material 50 having a small mass will exhibit a high rate of rise of temperature proportionate to an increase in current, voltage or power. In each case, the change in temperature is also related to a known thermal coefficient of resistance for the material of which electrically-conductive material 50 is composed. For the range of operation, the thermal coefficient of resistance as a function of temperature may be assumed to be known. Adaptive temperature controller 10 thereby avoids overshoot or undershoot of the desired temperature by determining in advance the responsiveness of electrically-conductive material 50 to changes in current, voltage or power. In an alternative embodiment, adaptive temperature controller 10 may include a look-up table of known materials used for electrically-conductive material 50 at various temperatures and include the appropriate thermal coefficient of resistance at the temperature of electrically-conductive material 50 to determine the associated temperature. In a further embodiment, adaptive temperature controller 10 may record the change in resistance as a function of the change in applied power throughout operation, thereby mapping the function throughout.

Adaptive temperature controller 10 may control or maintain one or more electrically conductive materials 50.

Further, adaptive temperature controller 10 may control an electrically-conductive material 50 to provide varying temperatures to a particular device or over a corresponding period of time, such as stepped or ramped temperature increases.

In a further embodiment, adaptive temperature controller 10 may be used in conjunction with a component 101 composed of an electrically-conductive material 50 such as nickel. Once the thermal coefficient of resistance of electrically-conductive material 50 is known, the temperature of component 101 may be controlled, such that the temperature may be increased at a stepped or fixed rate to provide increased separation between compounds having similar boiling points.

The adaptive temperature controller 10 configured to control the temperature of an electrically-conductive material 50 by determination of resistance and application of power, current or voltage provides several advantages over the prior art, particularly temperature controllers using heater cartridges. As no separate heater cartridge is required intermediate the heating element and the temperature controller, the mass of adaptive temperature controller 10 is less than that of such temperature controllers. Moreover, localized areas of increased or decreased temperature may be avoided as the heat flux is distributed over a large area, rather than emanating from a particular location associated with the heater cartridge. Further, the temperature may be more uniformly distributed since the heat is transferred from the surface along the length of the column 101 to provide an even distribution along its length rather than from one point associated with a cartridge heater. Finally temperature increases may be accomplished quite rapidly as the heat is generated within the electrically-conductive material 50 rather than transferred through a heat-conductive material from an exterior element.

Figure 4:
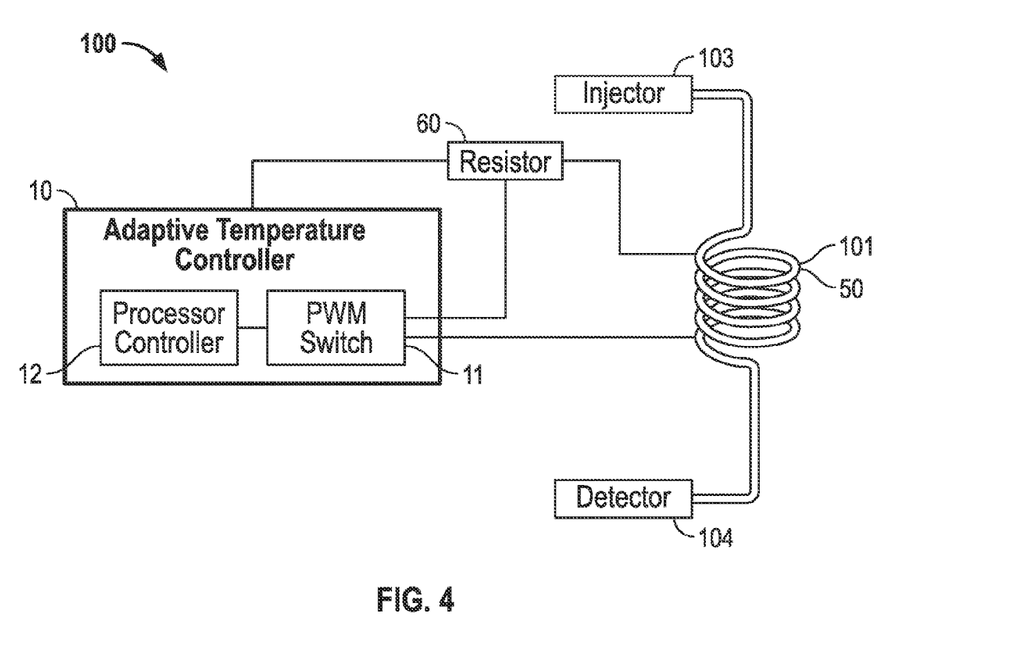
FIG. 4 depicts component 101 where heating is controlled by the adaptive temperature controller via a pulse-width-modulated switching supply controlled by a microcontroller/microprocessor.

As depicted in FIG. 4, in one embodiment, wherein component 101 is comprised of electrically-conductive material 50, power for producing heating is supplied by adaptive temperature controller 10. This may be via a pulse-width-modulated switching supply 11 controlled by a microcontroller/microprocessor 12, although other supply control systems known in the art may alternatively be used. The current supplied to electrically-conductive material 50 may be determined by detecting the voltage drop across a current-sense resistor 60, typically 0.1 Ohms, placed between the current supply and electrically-conductive material 50. Likewise the voltage across electrically-conductive material 50 is detected. Amplifiers to properly scale the detected voltages may be used before the representative signals are passed to analog-to-digital converters. The digitized signals thereby obtained, e.g. at 1000 times per second, are passed to a microcontroller wherein the relative resistance value is obtained by application of Ohm's Law, namely by dividing the converted voltage value by the converted current value. The relative resistance value may be compared against a reference resistance value for temperature control employing the conventional proportional-integral-derivative (PID) or another control algorithm. The temperature of electrically-conductive material 50 may also be determined for display or recording by solving the equation relating temperature to resistance well known in the art or interpolating a value from a table.

For temperature ramping, the detected signal from the current-sense circuit may be used to control the rate, linear, exponential or otherwise, of temperature change by virtue of controlling for constant current within electrically-conductive material 50.

Figure 5:
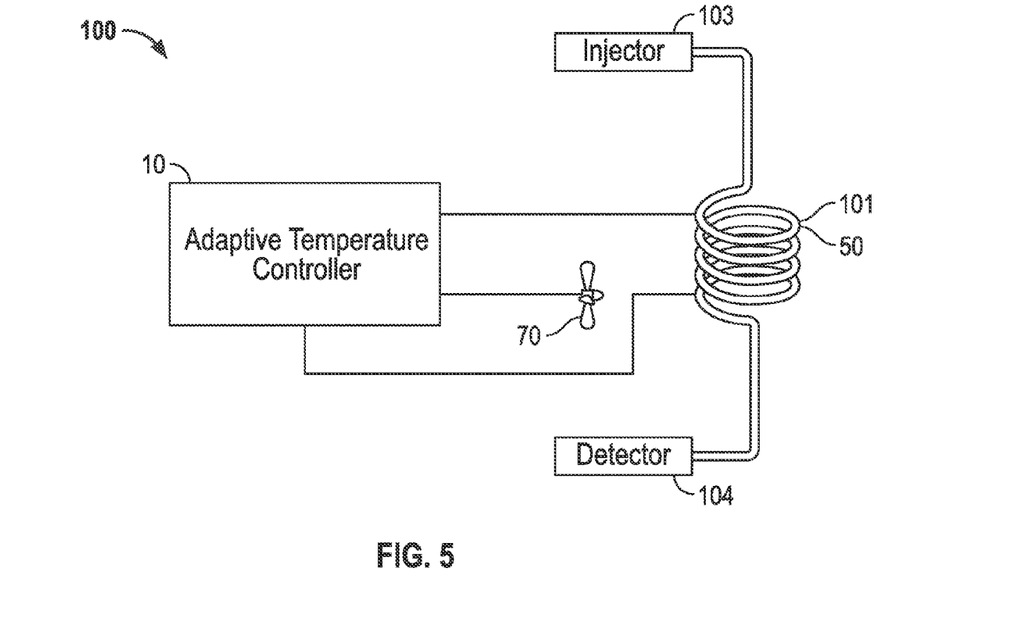
FIG. 5 depicts component 101 where heating and cooling is controlled by the adaptive temperature controller.

In a further embodiment, depicted in FIG. 5, an adaptive temperature controller 10 may be configured to control the temperature of electrically-conductive material 50 and a fan 70 which may induce air flow about component 101. Fan 70 may be used to increase the rate of cooling of component 101 and electrically-conductive material 50.

Figure 6:
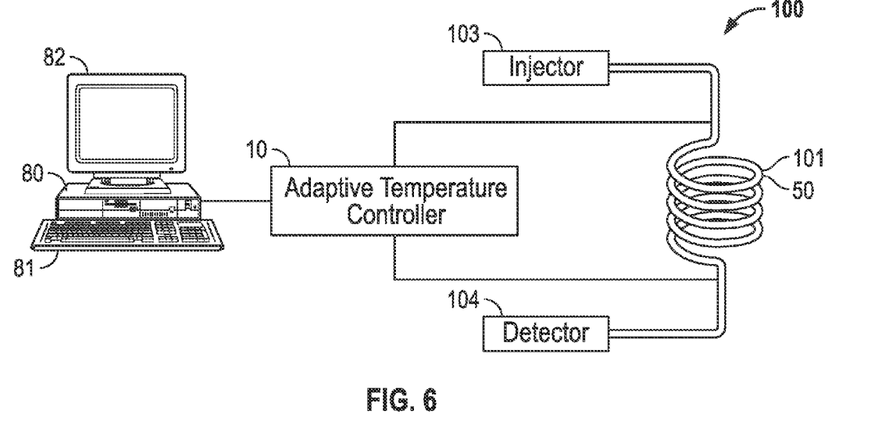
FIG. 6 depicts component 101 where heating is controlled by the adaptive temperature controller which includes a computer interface.
Figure 7:
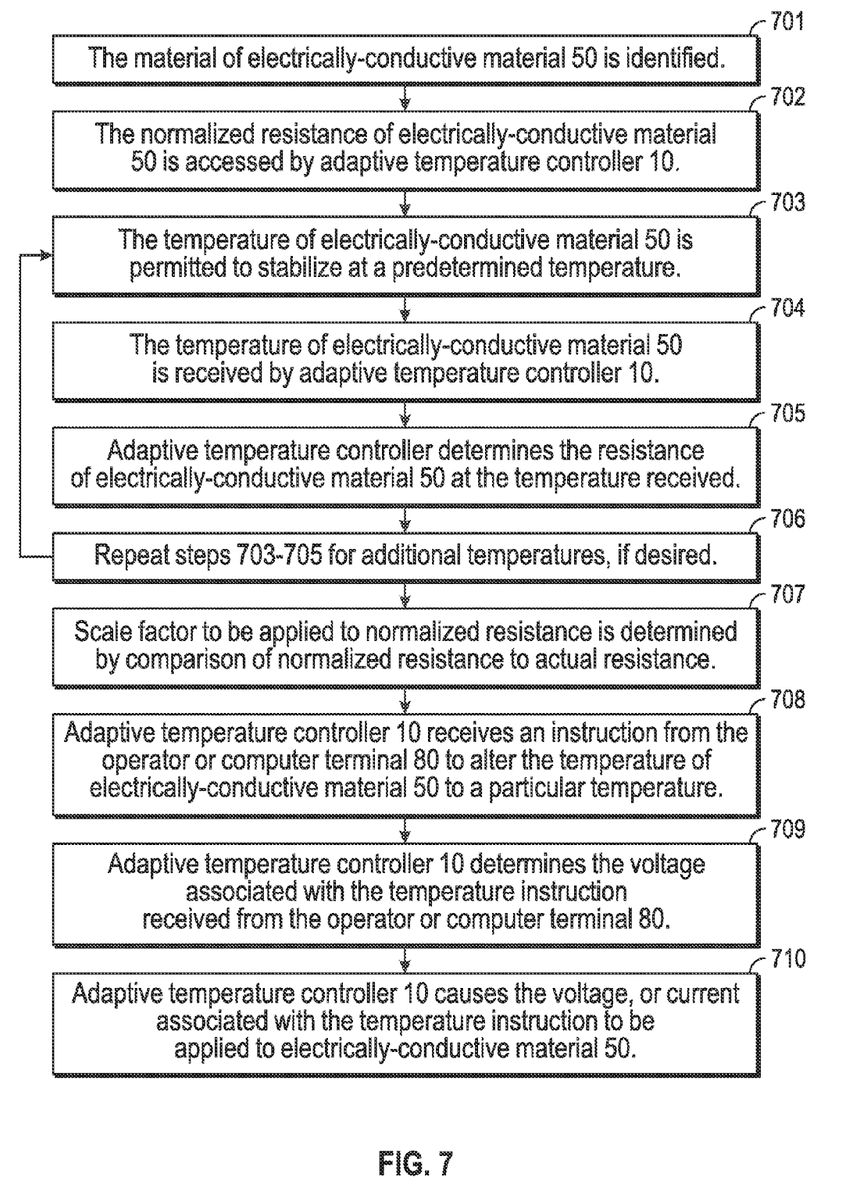
FIG. 7 depicts a flow diagram of one embodiment of the steps for calibration of the adaptive temperature controller with an electrically conductive material.

In a further embodiment, depicted in FIG. 6, adaptive temperature controller 10 includes a computer terminal 80. The computer terminal 80 provides an interface for control via a keyboard 81 and monitor 82. The computer terminal 80 may be any computer, including a conventional desktop computer or a handheld computer, such as those associated with Palm®, and electrically conductive material 50 calibration may be accomplished in the following steps, depicted in FIG. 7:

1) Step 701—The material, such as nickel, platinum, or copper of which electrically-conductive material 50 is composed is identified;
2) Step 702—The normalized resistance characteristic of the material from which electrically-conductive material 50 is composed is identified by adaptive temperature controller 10. This provides a normalized resistance characteristic for a pure sample of the material as a function of temperature. This normalized resistance characteristic, however, must be scaled to the actual resistance of electrically-conductive material 50 at a reference temperature to provide the applicable resistance characteristic for use by adaptive temperature controller 10;
3) Step 703—The temperature of electrically-conductive material 50 is permitted to stabilize at a predetermined temperature, which may be an elevated temperature close to that at which the electrically-conductive material 50 will be used;
4) Step 704—The temperature of electrically-conductive material 50 is received by adaptive temperature controller 10;
5) Step 705—Adaptive temperature controller 10 records the resistance of electrically-conductive material 50 at the temperature received. This may be accomplished by supplying at least once a voltage or current to electrically-conductive material 50 and measuring the voltage or current conducted therethrough or by any application of Ohm's Law. This may be accomplished directly by adaptive temperature controller 10 or by input from an external multimeter;
6) Step 706—Steps 703-705 are repeated for additional temperatures as elected;
7) Step 707—The scale factor to be applied to the normalized resistance characteristic associated with electrically conductive material 50 is determined by comparison of the normalized resistance characteristic to the actual resistance at a common temperature.
8) Step 708—Adaptive temperature controller 10 receives an instruction from the operator or computer terminal 80 to alter the temperature of electrically-conductive material 50 to a particular temperature;
9) Step 709—Adaptive temperature controller 10 determines the resistance associated with the temperature instruction received from the operator or computer terminal 80 based on the scaled normalized resistance characteristic;
10) Step 710—Adaptive temperature controller 10 causes the voltage, or current, associated with the temperature instruction to be applied to electrically-conductive material 50.

Figure 8:
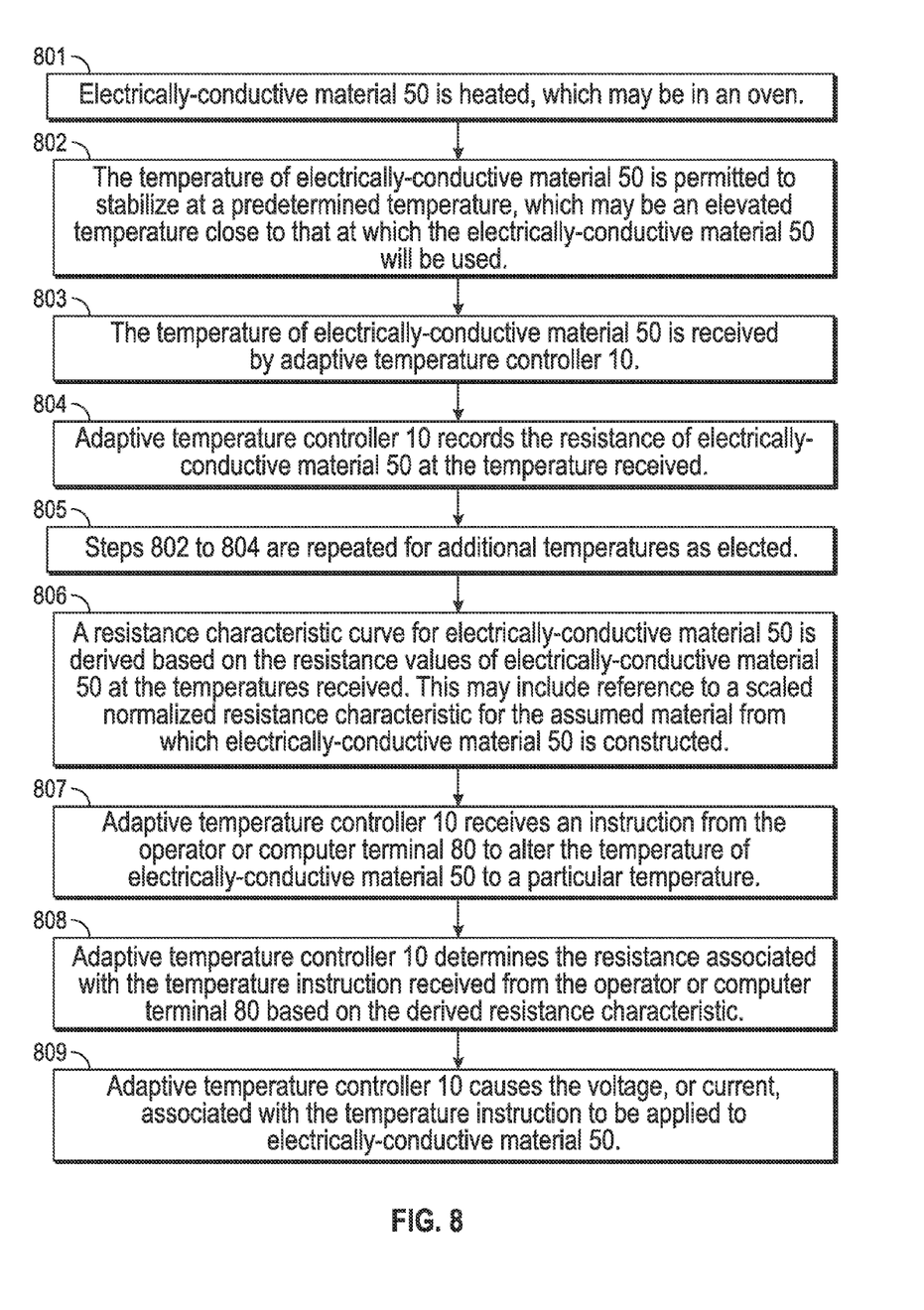
FIG. 8 depicts a flow diagram of an alternative embodiment of the steps for calibration of the adaptive temperature controller with an electrically conductive material.

Alternatively, electrically-conductive material 50 calibration may be accomplished by creation of a calibration for each electrically-conductive material 50. Such calibration may be particularly helpful where electrically-conduct material 50 is composed of a material containing impurities, such as nickel contaminated with cobalt. In such a situation, the normalized resistance characteristic of the pure material for nickel is not consistent with the resistance characteristic of the actual material. As a result, if the normalized resistance characteristic were used, the actual temperature of the electrically-conductive material 50 would differ from the temperature projected by adaptive temperature controller 10. Thus, generation of a specific resistance characteristic curve may provide more accurate data to be relied upon by adaptive temperature controller 10. As depicted in FIG. 8, these steps may include:

1) Step 801—Electrically-conductive material 50 is heated, which may be in an oven;
2) Step 802—The temperature of electrically-conductive material 50 is permitted to stabilize at a predetermined temperature, which may be an elevated temperature close to that at which the electrically-conductive material 50 will be used;
3) Step 803—The temperature of electrically-conductive material 50 is received by adaptive temperature controller 10;
4) Step 804—Adaptive temperature controller 10 records the resistance of electrically-conductive material 50 at the temperature received.
5) Step 805—Steps 802 to 804 are repeated for additional temperatures as elected;
6) Step 806—A resistance characteristic curve for electrically-conductive material 50 is derived based on the resistance values of electrically-conductive material 50 at the temperatures received. This may include reference to a scaled normalized resistance characteristic for the assumed material from which electrically-conductive material 50 is constructed.
7) Step 807—Adaptive temperature controller 10 receives an instruction from the operator or computer terminal 80 to alter the temperature of electrically-conductive material 50 to a particular temperature;
8) Step 808—Adaptive temperature controller 10 determines the resistance associated with the temperature instruction received from the operator or computer terminal 80 based on the derived resistance characteristic;
9) Step 809—Adaptive temperature controller 10 causes the voltage, or current, associated with the temperature instruction to be applied to electrically-conductive material 50.

Figure 9:
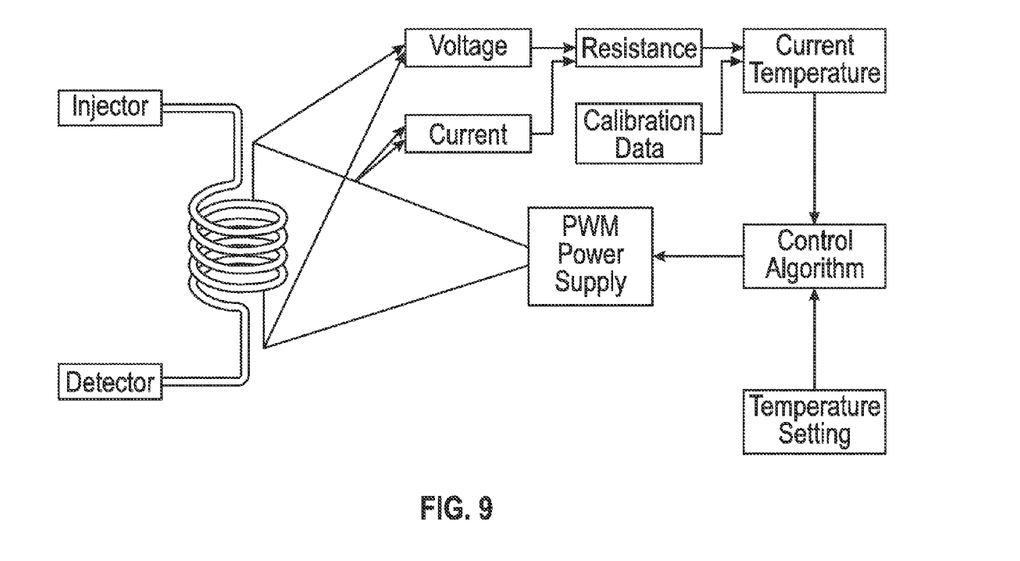
FIG. 9 depicts an embodiment of the system.

One embodiment of the adaptive temperature controller 10 as part of a larger chromatographic system is illustrated in FIG. 9. As illustrated, the adaptive temperature controller 10 receives a temperature setting input and by application of a control algorithm based on the current temperature (as determined from resistance, identified from measurement of current and voltage, as an indicator of temperature, based on the calibration data), causes a PWM power supply to supply sufficient current to electrically-conductive material 50, here a component 101, namely a column, to be heated or to cool as necessary.

The terms and expressions which have been employed in the foregoing specification are used therein as terms of description and not of limitation, and there is no intention, in the use of such terms and expressions, of excluding equivalents of the features shown and described or portions thereof.

We claim:

1. An adaptive temperature controller system for chromatographic analysis to control and maintain the temperature of a chromatographic column assembly during heating of said chromatographic column assembly, comprising:
    said chromatographic column assembly including a circular coil of a fused silica chromatographic column and a metal wire, said fused silica chromatographic column and said metal wire maintained adjacent within said coil, said coil wrapped in a heat conductive outer jacket; and
    an adaptive temperature controller having
        a device for measuring resistance,
            said device for measuring resistance recording measurement of two members of the group consisting of power, current and voltage through said metal wire, and
            said device for measuring resistance determining resistance of said metal wire by application of Ohm's Law to said two members of the group consisting of power, current and voltage;
        a device for determining responsiveness of resistance,
            said device for determining responsiveness of resistance determining the change in said resistance of said metal wire relative to change in said two members of the group consisting of power, current and voltage;
        a power supply,
            said power supply in electrical communication with said metal wire;
        said metal wire altering temperature based on said electrical communication from said power supply;
        a device for controlling the output of said power supply,
            said device for measuring resistance outputting said determination of the resistance of said metal wire to said device for controlling the output of said power supply;
        said device for determining responsiveness of resistance outputting said determination of the change in said resistance of said metal wire relative to change in said two members of the group consisting of power, current and voltage to said device for controlling the output of said power supply;
        said device for controlling the output of said power supply determining the thermal coefficient of resistance of said metal wire based on the output of said device for measuring resistance and a temperature input; and
        said device for controlling the output of said power supply controlling the temperature of said metal wire based on the output of one of the group of power, voltage or current.

2. The adaptive temperature controller of claim 1 wherein said wire is composed of nickel.

3. The adaptive temperature controller of claim 1 wherein said wire is composed of an alloy containing nickel.

4. The adaptive temperature controller of claim 1 further comprising a fan to induce air flow about said component.

5. The adaptive temperature controller of claim 1 wherein said adaptive temperature controller communicates with a computer.

6. The adaptive temperature controller of claim 2 wherein said adaptive temperature controller communicates with a computer.

7. A method for operation of an adaptive temperature controller system to control and maintain the temperature of said chromatographic column assembly during heating of a chromatographic column assembly, said adaptive temperature controller system including:
    a chromatographic column assembly, said chromatographic column assembly including a coil of a fused silica chromatographic column and a metal wire, said fused silica chromatographic column and said metal wire maintained adjacent within said coil, said coil wrapped in a heat conductive outer jacket; and
an adaptive temperature controller having
   a device for measuring resistance,
      said device for measuring resistance recording measurement of two members of the group consisting of power, current and voltage through said metal wire, and
      said device for measuring resistance determining resistance of said metal wire by application of Ohm's Law to said two members of the group consisting of power, current and voltage;
   a device for determining responsiveness of resistance,
      said device for determining responsiveness of resistance determining the change in said resistance of said metal wire relative to change in said two members of the group consisting of power, current and voltage;
   a power supply,
      said power supply in electrical communication with said metal wire;
   said metal wire altering temperature based on said electrical communication from said power supply;
   a device for controlling the output of said power supply,
      said device for measuring resistance outputting said determination of the resistance of said metal wire to said device for controlling the output of said power supply;
   said device for determining responsiveness of resistance outputting said determination of the change in said resistance of said metal wire relative to change in said two members of the group consisting of power, current and voltage to said device for controlling the output of said power supply;
   said device for controlling the output of said power supply determining the thermal coefficient of resistance of said metal wire based on the output of said device for measuring resistance and a temperature input; and
   said device for controlling the output of said power supply controlling the temperature of said metal wire based on the output of one of the group of power, voltage or current;
comprising:
said adaptive temperature controller identifying the normalized resistance characteristic of said metal wire;
permitting the temperature of said metal wire to stabilize at a predetermined temperature;
said adaptive temperature controller receiving the temperature of said metal wire;
said adaptive temperature controller receiving a resistance at a temperature associated with a temperature input of said metal wire;
said adaptive temperature controller determining a scale factor to be applied to said normalized resistance characteristic by comparison of said normalized resistance characteristic to said resistance at a temperature associated with a temperature input;
said adaptive temperature controller receiving an instruction to alter the temperature of said metal wire to a particular temperature;
said adaptive temperature controller receiving an instruction to alter the temperature of said metal wire to a particular temperature;
said adaptive temperature controller determining the voltage or current associated with the temperature instruction received; and
said adaptive temperature controller causing one of the group of voltage and current associated with the temperature instruction to be applied to said metal wire based on said responsiveness of resistance of said metal wire to heat said chromatographic column.

8. A method for operation of an adaptive temperature controller system to control and maintain the temperature of a system component during heating of said system component, for use with an electrically-conductive material to heat a system component, said adaptive temperature controller including:
   a chromatographic column assembly, said chromatographic column assembly including a coil of a fused silica chromatographic column and a metal wire, said fused silica chromatographic column and said metal wire maintained adjacent within said coil, said coil wrapped in a heat conductive outer jacket; and
   an adaptive temperature controller having
      a device for measuring resistance, said device for measuring resistance recording measurement of two members of the group consisting of power, current and voltage through said metal wire;
      said device for measuring resistance determining resistance of said metal wire by application of Ohm's Law to said two members of the group consisting of power, current and voltage;
      a device for determining responsiveness of resistance, said device for determining responsiveness of resistance determining the change in said resistance of said metal wire relative to change in said two members of the group consisting of power, current and voltage;
      a power supply, said power supply in electrical communication with said metal wire;
      said metal wire altering temperature based on said electrical communication from said power supply;
      a device for controlling the output of said power supply, said device for measuring resistance outputting said determination of the resistance of said metal wire to said device for controlling the output of said power supply;
      said device for determining responsiveness of resistance outputting said determination of the change in said resistance of said metal wire relative to change in said two members of the group consisting of power, current and voltage to said device for controlling the output of said power supply;
      said device for controlling the output of said power supply determining the thermal coefficient of resistance of said metal wire based on the output of said device for measuring resistance and a temperature input; and
   said device for controlling the output of said power supply controlling the temperature of said metal wire based on the output of one of the group of power, voltage or current;
comprising:
   heating said metal wire;
   permitting the temperature of said metal wire to stabilize at a predetermined temperature;
   receiving said temperature as a temperature input;
   determining the resistance of said metal wire at said temperature;
   deriving a resistance characteristic curve for said metal wire from said identification of said resistance at the temperature received;
   receiving an instruction to alter the temperature of said metal wire;

determining the resistance associated with the said instruction from said resistance characteristic curve; and causing the voltage or current associated with the instruction to be applied to said metal wire to heat said chromatographic column.

\* \* \* \* \*